United States Patent [19]

Shannon et al.

[11] Patent Number: 5,003,811
[45] Date of Patent: Apr. 2, 1991

[54] SHOCK TESTING APPARATUS

[75] Inventors: Leland K. Shannon, San Diego; Ted L. Gentry; Toby Le, both of Poway, all of Calif.

[73] Assignee: Cubic Defense Systems, San Diego, Calif.

[21] Appl. No.: 345,098

[22] Filed: Apr. 28, 1989

[51] Int. Cl.$^5$ .............................................. G01N 3/30
[52] U.S. Cl. ........................................................ 73/12
[58] Field of Search ................................. 73/12, 844

[56] References Cited

U.S. PATENT DOCUMENTS

| | | |
|---|---|---|
| 2,799,824 | 7/1957 | Heynick et al. . |
| 3,157,046 | 11/1964 | Orner . |
| 3,200,634 | 8/1965 | Rickards . |
| 3,209,585 | 10/1965 | Wolstenholme et al. . |
| 3,285,060 | 11/1966 | Pessen . |
| 3,557,603 | 1/1971 | Carr . |
| 3,580,056 | 5/1971 | Warner . |
| 4,034,602 | 7/1977 | Woo et al. . |
| 4,085,609 | 4/1978 | Kelly . |
| 4,295,374 | 10/1981 | Kusy . |
| 4,402,210 | 9/1983 | Vandeberg . |
| 4,405,243 | 9/1983 | Kuraoka et al. . |
| 4,442,697 | 4/1984 | Jones et al. . |

OTHER PUBLICATIONS

Kuznetsov et al, "Shock-Test Stand", Sov. J. Opt. Technol 45(11), Nov. 1978, pp. 704-705.
High G Pyrotechnic Shock Simulation Using Metal-to-Metal Impact, by Monty Bai and Wesley Thatcher, Motorola Government Electronics Division "Shock and Vibration Bulletin No. 49, Par II, S.V.K.", Sep., 1979.
Pyrotechnic Shock Simulation Using the Controlled Response of a Resonating Bar Fixture, by Neil T. Davie, "Proceedings-Institute of Environmental Sciences", Apr. 15, 1985, pp. 344-351.

Primary Examiner—Charles A. Ruehl
Attorney, Agent, or Firm—Brown, Martin, Haller & McClain

[57] ABSTRACT

A shock testing apparatus for simulating pyrotechnic shocks comprises an elongate bar suspended for movement in a longitudinal direction, and a pendulum hammer suspended for impact with one end of the bar to excite it into longitudinal resonance. A mounting assembly at the opposite end of the bar allows test components to be mounted in three perpendicular x, y and z orientations relative to the bar. A reversible drive motor raises the hammer to a predetermined height under the control of a control assembly which switches off the motor to allow release of the hammer when the predetermined height is reached. Damping masses are clamped at pre-selected positions along the bar to produce a predetermined shock response spectrum on impact with the hammer.

27 Claims, 12 Drawing Sheets

SHOCK TESTING APPARATUS

BACKGROUND OF THE INVENTION

The present invention relates generally to a shock testing apparatus, and more particularly to a shock testing apparatus designed to simulate pyrotechnic shock (high g short duration) conditions.

Aerospace systems and components often experience pyrotechnic shock conditions as a result of adjacent explosions, for example during separation of stages during flight. As a result of this, components for aerospace systems must normally undergo pyrotechnic shock testing prior to acceptance. There are three basic techniques for pyrotechnic shock testing, all of which have advantages and disadvantages. One technique uses an electrodynamic shaker to produce a desired shock spectrum. However, the amplitude and event duration is limited by the capacity of the shaker. Also, this technique is typically fairly expensive. Another technique employs actual explosives to produce the desired shock. This has the obvious disadvantage of using relatively expensive explosives for each test, and also may have poor repeatability. Finally, mechanical impact techniques may be used to simulate the pyrotechnic shock conditions. In the past, these techniques have also been subject to poor controllability and repeatability.

One known mechanical impact technique for simulating a pyrotechnic shock involves suspending an elongate, metallic beam and exciting it into longitudinal resonance by impact at one end of the beam with a pendulum hammer. Test items are attached to the beam in three orthogonal orientations successively, corresponding to impacts in the x, y and z axis orientations, and the shock response spectrum of the beam is calculated from the measured acceleration using suitably positioned accelerometers. One problem with this is that it does not provide control of the shock response spectrum, or allow any easy means for varying the spectrum to meet alternative test requirements. Normally, different applications require different standard spectra for acceptance testing. Also, peaks are encountered in the response spectrum at the resonant frequencies of the beam. The peaks will normally be outside the allowed tolerance levels of the standard test spectrum, which is generally smooth. This makes it difficult, if not impossible, to generate a wide variety of requested shock spectra.

One previously proposed method of controlling the spectra produced by a resonant bar fixture is to clamp weights at the longitudinal nodal locations of one of the modal frequencies of the bar. The theory predicts that masses clamped at the nodes of the ith mode will cause the response to be dominated by the ith mode.

SUMMARY OF THE INVENTION

It is an object of the present invention to provide an improved shock testing apparatus for simulating pyrotechnic shocks.

According to the present invention, a shock testing apparatus is provided which comprises an elongate beam suspended to allow movement in the longitudinal direction (free-free), an impacting device such as a pendulum hammer for impacting the beam at one end, and a mounting assembly at the opposite end of the beam for mounting a component to be tested on the beam in any of three orthogonal orientations relative to the beam, the orientations corresponding to perpendicular x and y axis directions in a plane parallel to the component base and a z axis direction normal to the component base. Sensors, e.g. accelerometers, are provided on the mounting assembly for sensing oscillation of the beam as a result of impact by the pendulum hammer. A control assembly is provided for controlling the impact velocity. In the case of a pendulum hammer, a drive assembly is provided for raising the pendulum hammer to a predetermined height, and a control system is provided for releasing the hammer when the predetermined height is reached. Masses are clamped across the beam at predetermined intervals along the beam to produce a predetermined shock transient and associated shock response spectrum.

The control of the position at which the hammer is released allows a predictable shock response spectrum to be repeated reliably for each orientation of a test component and for subsequent test components. The positioning of the masses will depend on the desired shock response spectrum. However, for a smooth spectrum with no peaks outside preselected tolerance levels, masses are preferably clamped close to, but not on, at least some of the anti-node positions of the fundamental frequency and one or more of its harmonics. In one specific embodiment, masses were positioned close to the anti-node positions of the first four harmonics of the beam. This involves first exciting the beam to determine the harmonic frequencies and the node anti-node positions at each frequency, subsequently positioning masses close to the anti-node positions and generating shock response spectra. The mass positions can be adjusted or tuned until the desired spectrum is produced.

By positioning masses close to but not on the anti-nodes (or peaks) of a particular resonant frequency, the peak in the response spectrum at that frequency can be damped or reduced. The masses should not be clamped on the anti-node position, since the response at that frequency would then be eliminated, producing a pronounced dip in the spectrum at that point. By positioning masses close to but not on the anti-nodes at each of the harmonic frequencies measurable on the beam, a much smoother spectrum within desired limits can be achieved.

Preferably, a braking mechanism is provided for stopping the hammer after its first impact on the beam, so that it does not rebound and again strike the beam. Since the hammer height on release is controlled, the spectrum amplitude can be controlled and repeated for subsequent tests, providing consistency in the test results.

In the preferred embodiment of the invention, the mounting assembly is welded at the end of the beam, and includes a threaded hole pattern for mounting a test component at the end of the beam with its base perpendicular to the longitudinal axis of the beam for z-axis response testing, and an extension plate for securing at the end of the beam with a threaded hole pattern for mounting a test component in two perpendicular orientations orthogonal to the z axis. This avoids mounting the test components on the beam itself, which will take up space which is needed for positioning the response damping masses. Sensors such as accelerometers will be mounted on the extension plate and on the end face of the beam for detecting and measuring the response during a series of component tests.

Preferably, the control system can be adjusted to allow the height at which the hammer is released to be varied, thus varying the amplitude of the response spectrum. In the preferred embodiment, the control system includes a reversible motor for driving the hammer up and down, a detector for detecting the height of the hammer, and a control circuit for comparing the hammer height with a preselected release height and allowing the hammer to be released only when that height is reached. The hammer release may be by means of a manually operated release switch which is enabled only when the hammer is at the correct height. Preferably, the control circuit also provides a maximum and minimum height limit for the hammer so that the hammer cannot be driven above a predetermined maximum height or below a minimum height. The minimum height preferably corresponds to the lowermost, vertical position of the hammer, to avoid damage to the beam, while the maximum height will be varied according to the ceiling height, to avoid any damage to the ceiling of the room in which the test apparatus is located.

This apparatus provides an improved technique for pyrotechnic shock simulation testing which is reliable, relatively inexpensive, and repeatable, and which can be tuned to a desired shock response spectrum relatively easily.

BRIEF DESCRIPTION OF THE DRAWINGS

The present invention will be better understood from the following detailed description of a preferred embodiment, taken in conjunction with the accompanying drawings, in which like reference numerals refer to like parts, and in which.

DESCRIPTION OF THE PREFERRED EMBODIMENT

Figure 1:
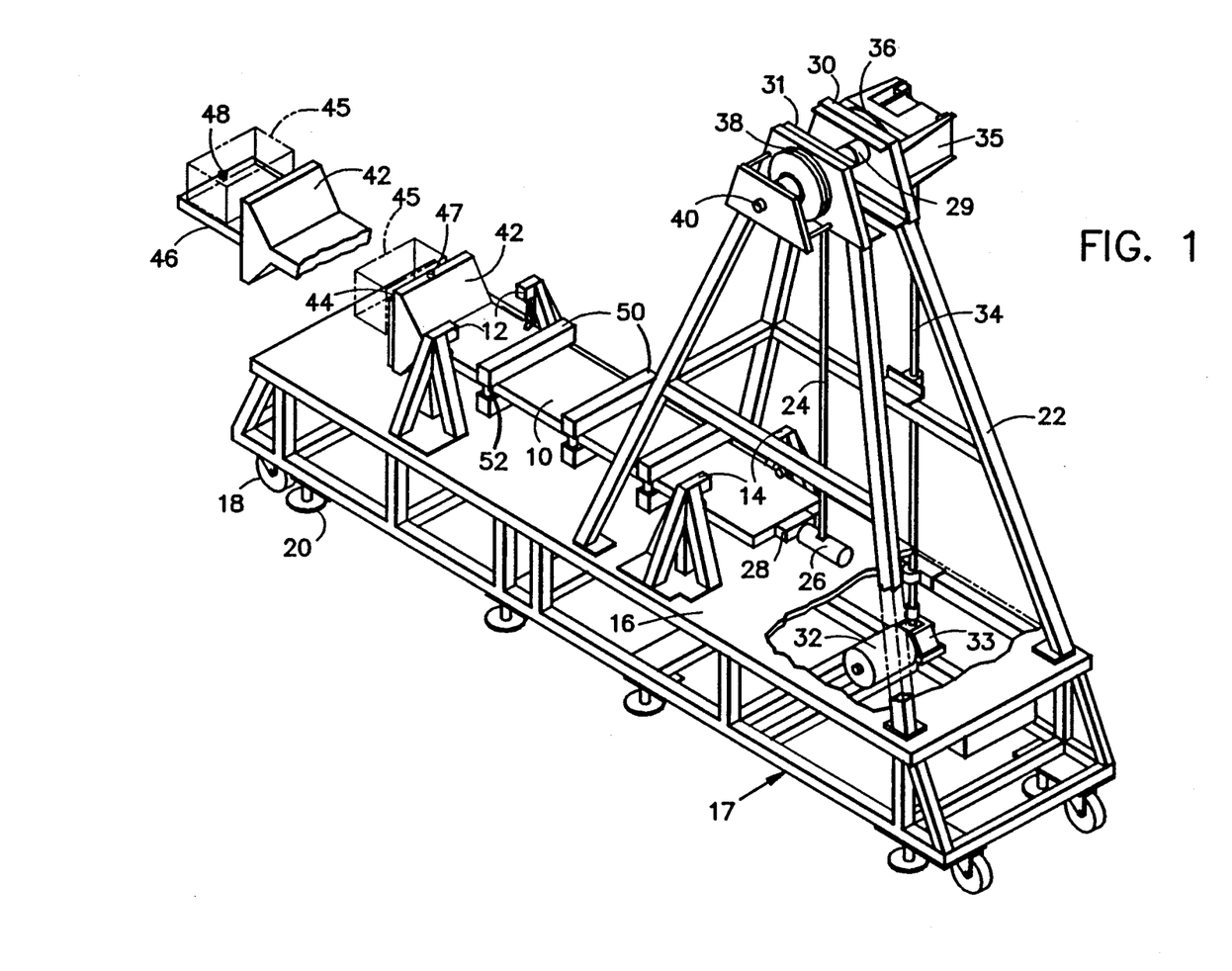
FIG. 1 is a perspective view of a pyrotechnic shock simulation testing apparatus according to a preferred embodiment of the present invention.

FIG. 1 illustrates a pyrotechnic shock simulation testing facility according to a preferred embodiment of the present invention. A flat elongate beam 10 is suspended horizontally from two pairs of spaced tripodal supports 12,14 allowing movement in a longitudinal direction. The supports are mounted on a suitable base plate or table 16 which is itself mounted on base frame 17. The base frame has caster wheels 18 to allow movement of the facility when necessary. Adjustable leveling supports 20 are provided for leveling the facility when located at a desired location. A pendulum support frame 22 projects upwardly from one end of the table 16, and a pendulum arm 24 is suspended from the top of frame 22 with a weight such as a hammer 26 secured at the lower end of the arm 24 for impact with one end of the beam 10. A suitable impact plate 28 is mounted at the impact end of the beam to protect the beam from damage. In the preferred embodiment of the invention hammer 26 is releasably secured to the arm, and a series of different weight hammers are provided to allow varying impulsive forces to be applied to the beam. For example, hammers ranging from 4 to 26 lbs. weight may be provided.

The upper end of the hammer is secured to a shaft 29 rotatably mounted at the top of frame 22 between end plates 30 and 31. Shaft 29 is driven by reversible drive motor 32 connected to shaft 29 via lower gear box 33, drive shaft 34, upper gear box 35 and clutch 36. A suitable braking device 38 is mounted on shaft 29 for holding the arm at a selected height, as will be explained in more detail below. A location sensor 40 senses movement of shaft 29 to determine the hammer position. In the preferred embodiment of the invention, sensor 40 comprises a potentiometer mounted on shaft 29 so that its output is dependent on the angular rotation of shaft 29, and thus the height of hammer 26.

The opposite end of the beam has an expanded head 42 with a flat end face 44 perpendicular to the longitudinal axis of the beam. The end face 44 has a suitable pattern of mounting bolt holes (not shown) to allow mounting of test components 45 directly on the end face for z- or vertical axis testing, or alternatively to allow mounting of extension or adapter plate 46 on the end face. Extension plate 46 extends coaxially from beam 10 and perpendicular to end face 44 to facilitate mounting of a component under test in the two horizontal or x and y axes, and will have a suitable bolt hole pattern to allow mounting of the component. In the preferred embodiment, end face 44 of the beam and extension plate 46 each have a universal 2×2 inch bolt hole mounting pattern. Suitable sensing devices such as accelerometers 47, 48 for sensing acceleration of the beam after hammer impact are mounted on both the end face 44 and the extension plate 46, as illustrated in FIG. 1.

A series of masses 50 are adjustably clamped at spaced locations along the beam 10 to allow tuning of the beam shock response spectrum, as will be explained in more detail below. Each mass consists of a pair of opposed parallel bars clamped together at opposite ends across opposite faces of the beam via bolts 52 or the like. The masses will be positioned on the beam prior to actual testing according to the desired shock response spectrum, and then clamped at the selected positions to test all components for which that particular shock response spectrum is required.

In one preferred example of the apparatus, a light weight magnesium beam of dimensions 15 by 2 by 77 inches with a 15 by 15 by 6 inch beveled end mounting plate was used. Magnesium alloy AZ-31B was selected for the beam because it requires less energy for excitation than either steel or aluminum, and also because of its excellent damping characteristics. Each clamp consisted of a pair of 2 by 2 by 17 inch aluminum bars clamped tightly on opposite side faces of the beam to ensure good physical contact with the beam. The pendulum arm was 6 feet long, and a case hardened 4140 alloy steel hammer was secured at the end of the arm, with a polyurethane insert to shock isolate the hammer from the pendulum arm. The impact surface of the hammer is preferably rounded to eliminate or reduce alignment problems. The impact plate may be of any selected material depending on the desired impact. In the preferred embodiment aluminum impact plates were used, but steel or other materials may alternatively be used for the impact plates.

Figure 2:
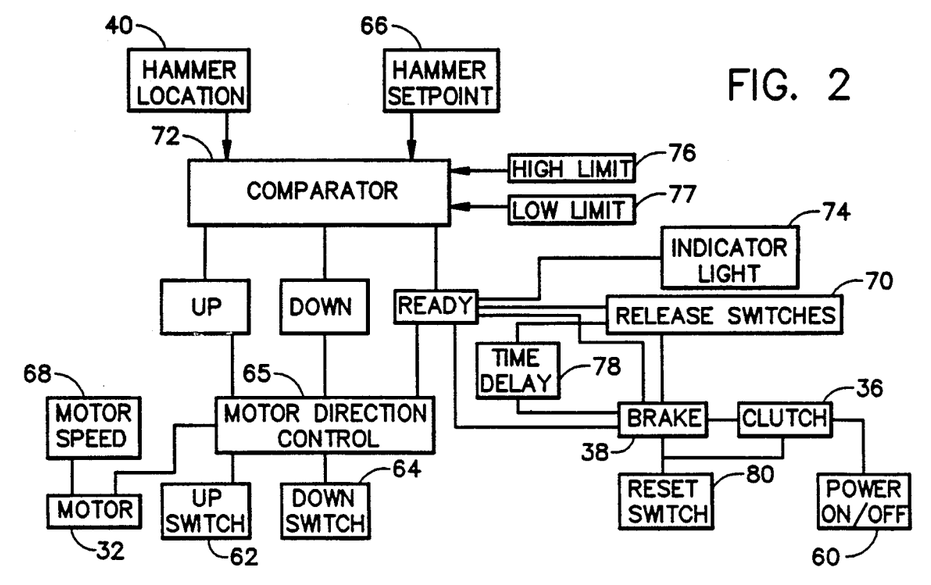
FIG. 2 is a block diagram showing the control system for controlling hammer positioning and release.
Figure 3A:
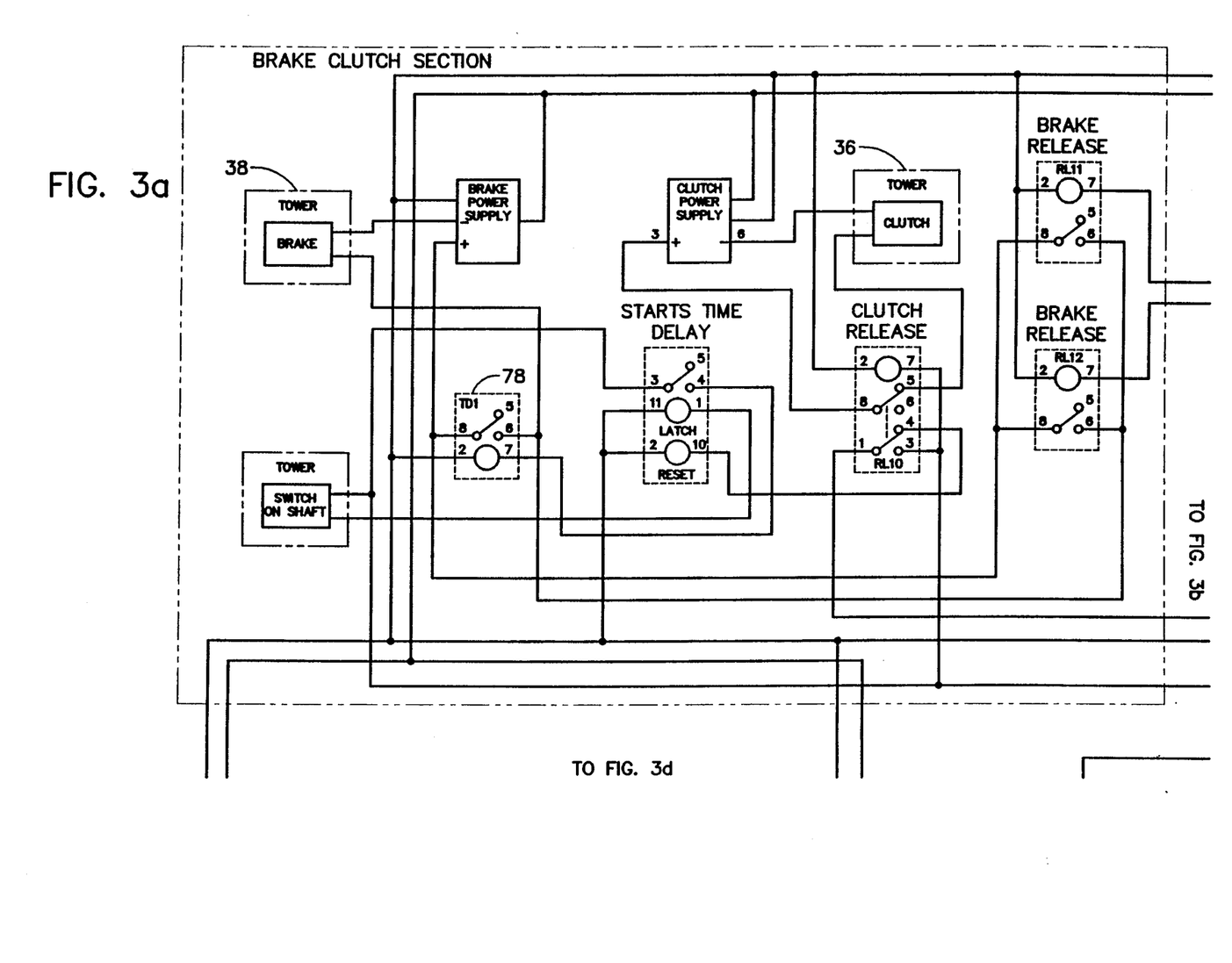
FIGS. 3A, B, C and D are schematics illustrating parts of one possible circuit for controlling the hammer as illustrated in FIG. 2.
Figure 3B:
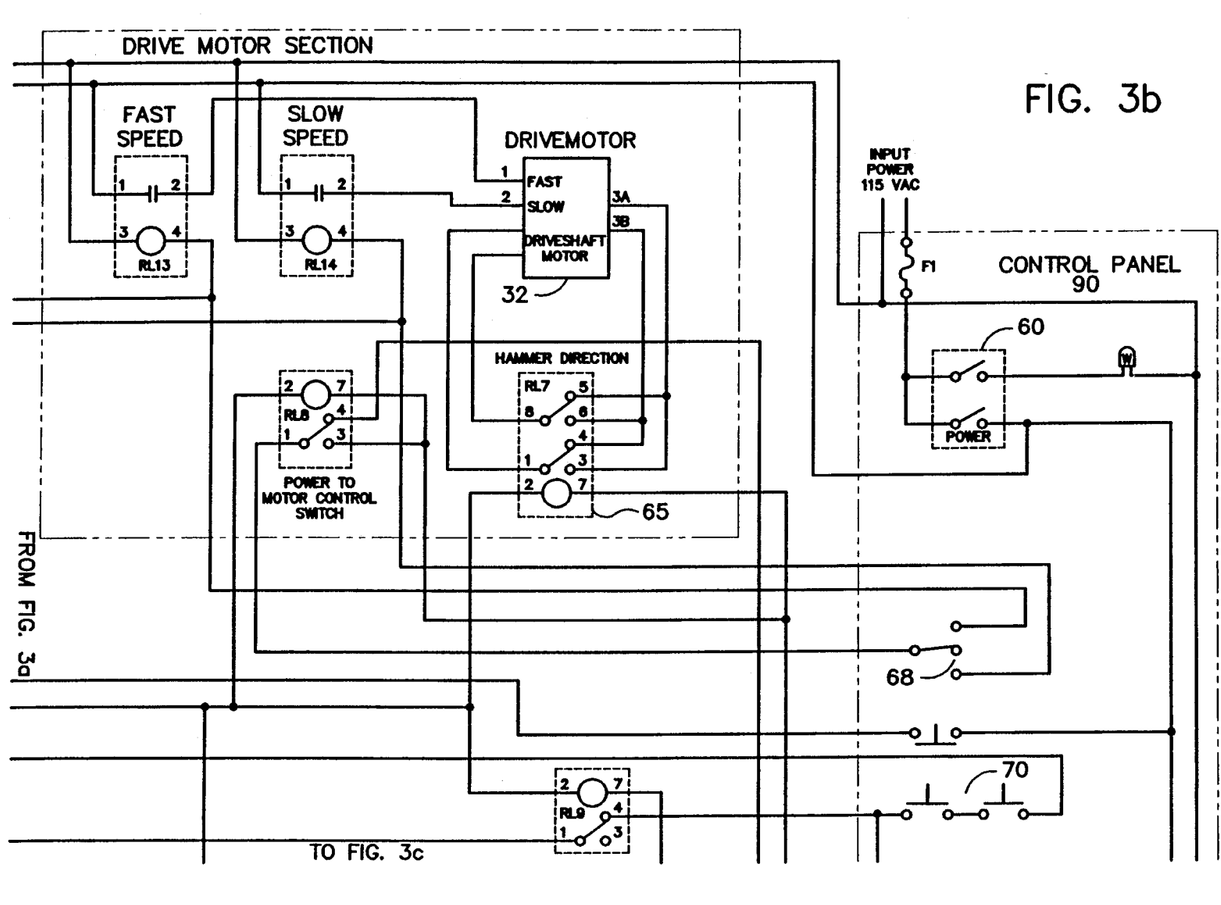
Figure 3C:
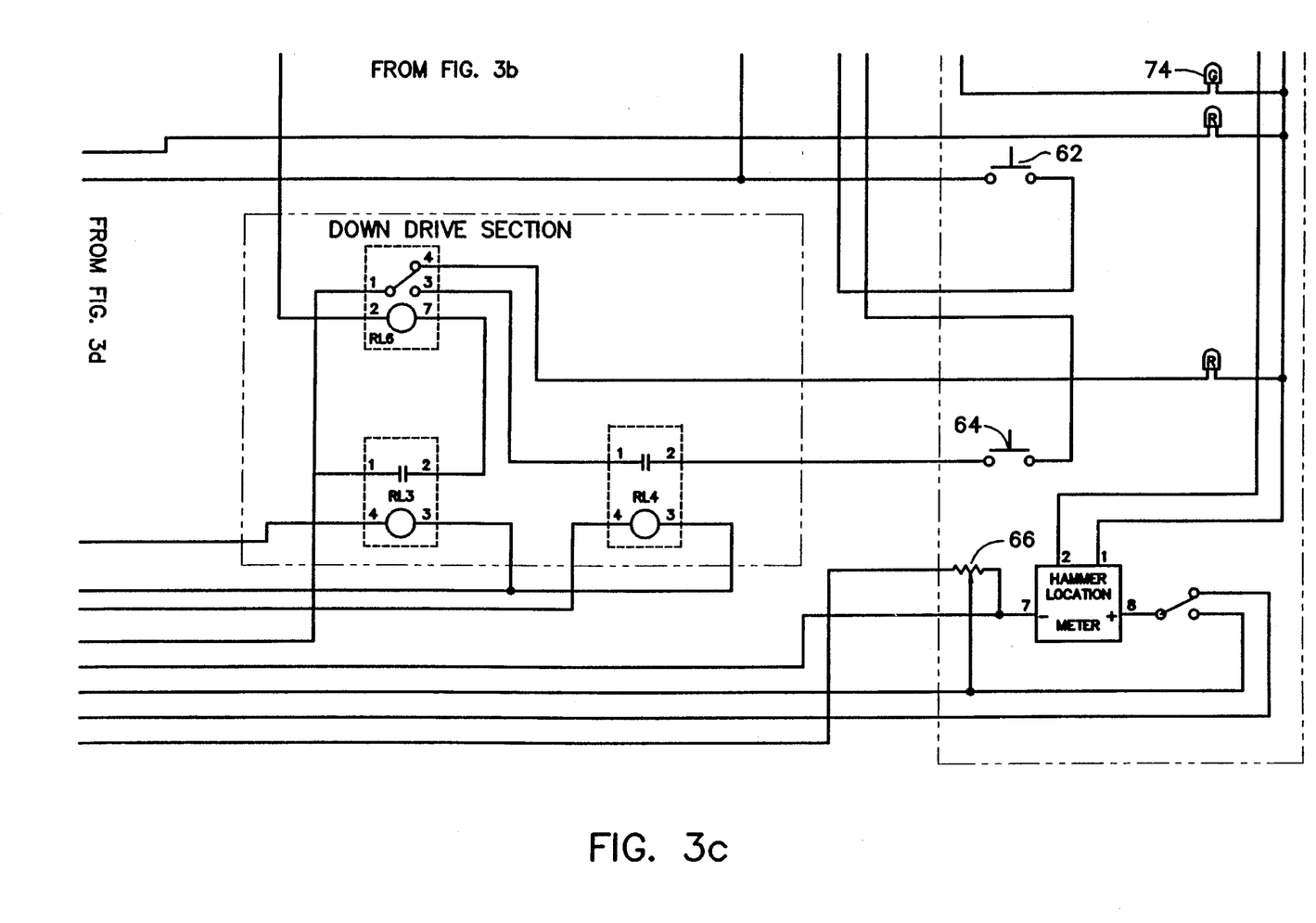
Figure 3D:
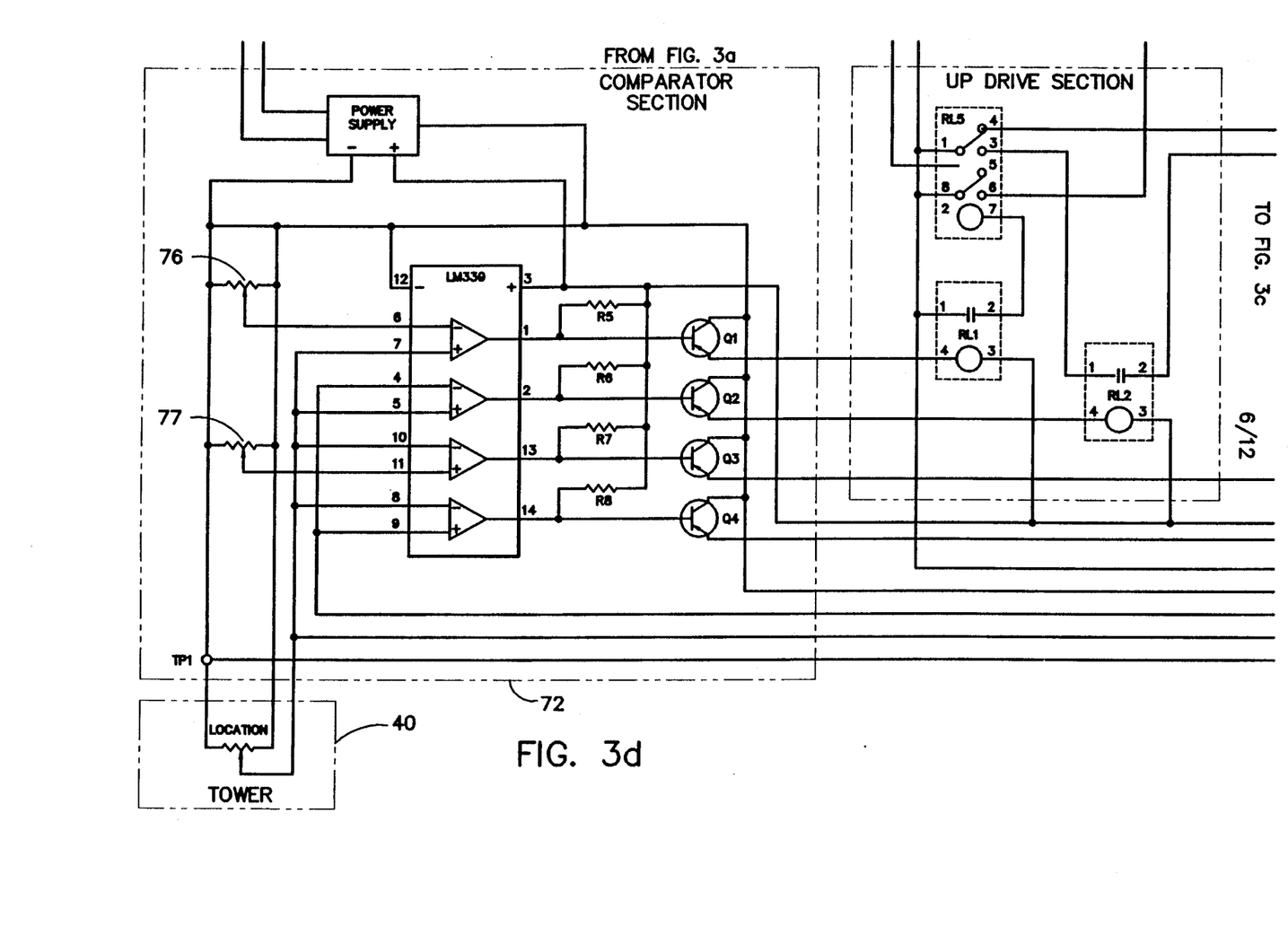
Figure 4:
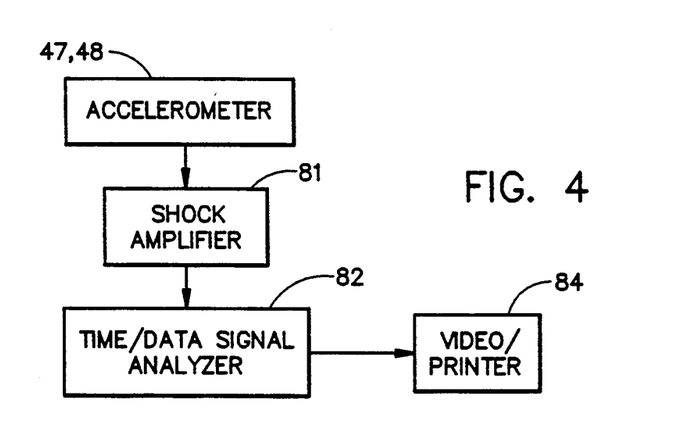
FIG. 4 is a block diagram illustrating instrumentation for producing a shock response spectrum.

Control of the operation of the test facility will be provided at a remote control panel. FIGS. 2 and 3 schematically illustrate the system for controlling hammer positioning and release, and FIG. 4 illustrates the instrumentation for generating a shock response spectrum from the accelerometer output. FIG. 2 is a block diagram of the control system. The control panel includes a power switch 60 for switching the facility on and off, hammer up and hammer down switches 62,64 for controlling motor controller 65 which activates the motor direction to drive the hammer up and down, a manually controlled height adjustment potentiometer 66 for adjusting the height at which the hammer is released, a speed control selector switch 68 for controlling the drive motor speed, and one or more hammer release switches 70. Preferably, two release switches are provided in series, and both must be pressed simultaneously for the hammer to be released, for safety reasons.

Referring to FIG. 2, the potentiometer 66 on the control panel is used to control the height at which the hammer is released. The outputs of setpoint potentiometer 66 and hammer height sensing potentiometer 40 are compared by a suitable comparator assembly 72, which may include a quadcomparator I.C. as illustrated in FIG. 3. When the output voltages are different, the hammer is driven up or down as appropriate. As soon as the voltages are equal, power is removed from the drive motor and the electric brake 38 is engaged. At the same time, an indicator light 74 on the control panel is illuminated to indicate to the operator that the hammer has reached the selected position and is ready for release. The hammer may then be dropped by pushing the two release buttons simultaneously, disengaging the brake and clutch.

The control circuit is also provided with upper and lower limits 76,77 for the hammer, which may be set by the operator. This ensures that the hammer cannot be driven high enough to impact the ceiling of the room in which the facility is located, and cannot be driven beyond the vertical down position, potentially damaging the beam. These limits are also controlled by the quadcomparator, which compares the hammer height with the pre-set upper and lower limits as well as with the selected release height, and which turns off the power to the motor if either of the limits is reached. At the same time, suitable indicator lights on the control panel are lit to indicate that the limits have been reached.

The hammer can only be released by simultaneous manual pushing of two release buttons, reducing the risk of inadvertent hammer release, potential injury to personnel in the vicinity and potential damage to the component under test if it is not properly secured to the beam. When the hammer is released, it falls and strikes the end of the beam, exciting the beam into longitudinal resonance and producing a shock transient in the beam. The resultant shock response spectrum can be generated from the output of the accelerometer which measures the acceleration at the opposite end of the beam.

In order to ensure that the hammer does not rebound and strike the beam again, a time delay relay 78 is utilized to engage the brake after impact and preclude any "double-hits", which would over-test the component under test. The time delay relay may be initiated on release of the hammer or on detection of hammer impact. The timer may be initiated by hammer release, with the delay time being varied according to the height at which the hammer is released. For a hammer release at a 90 degree angle, in other words with the pendulum arm horizontal, a time period of 800 milliseconds was used in one example of the invention. The time period may be varied manually by the operator according to the height or angle selected for hammer release.

Alternatively, a suitable cam mechanism on shaft 29 may be used to detect the vertical or impact position of the hammer and activate a switch for starting the timer. The delay time is sufficient to ensure that the hammer has impacted the beam and rebounded to a sufficient distance to ensure that the beam itself cannot swing back and impact the braked hammer. In practice, the hammer is stopped when it is at least one inch away from the initial impact position, in other words within the time period when it has rebounded to a distance of at least one inch and before it swings back to the same one inch distance.

Manually operated reset switch 80 engages clutch 36 and disengages brake 38, allowing the hammer to be raised again to exactly the same position for a subsequent test.

FIGS. 3A to 3D are schematic diagrams illustrating one example of a circuit for controlling the pendulum as illustrated in the block diagram of FIG. 2. Clearly, many alternative circuits are possible for performing these functions. As illustrated in FIGS. 3A to 3D, the various control switches, adjustment dials and indicator lights are provided on a control panel 90 accessible to the operator.

Suitable instrumentation for generating the shock response spectrum is of a type known in the field, and is schematically illustrated in FIG. 4. In the preferred embodiment of the invention, the accelerometer output was connected via a shock amplifier 81 to a suitable data analyzer 82 for analyzing the data to produce a shock response spectrum. The analyzer output is connected to a video display and/or printer 84. In one example, a Scientific Atlanta model 1201 signal analyzer was used for generating the desired spectra. In the preferred arrangement, the accelerometers used were Kistler Model No. 8044, and were connected to the data analyzer via a Endevco Model No. 2740B shock amplifier.

Figure 5:
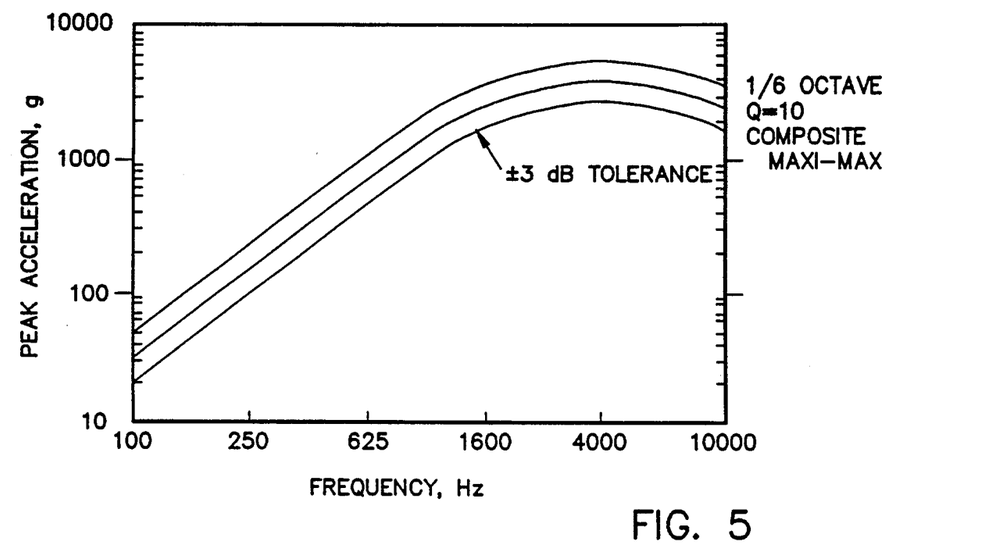
FIG. 5 is a diagrammatic illustration representing a typical pyrotechnic shock-response-spectrum standard with tolerances.
Figure 6:
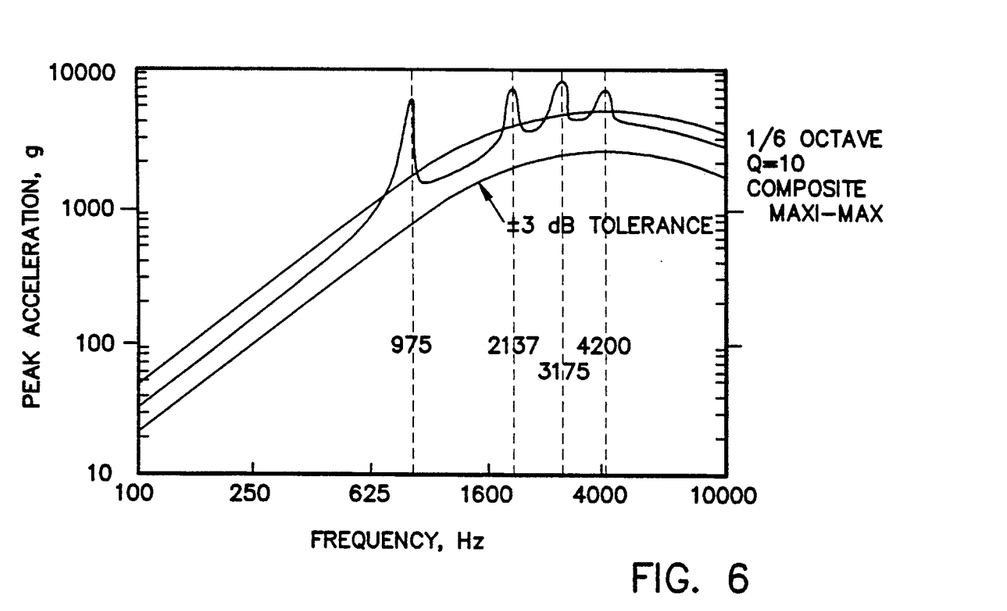
FIG. 6 illustrates the response spectrum produced by a typical beam mixture without any clamps.

In order to produce a desired shock response spectrum the beam is first tuned by suitably positioning the clamped masses. The tuning operation can best be understood with reference to FIGS. 5 to 15. FIG. 5 shows a typical shock response spectrum which may be required to meet pyrotechnic shock testing criteria for acceptance of test components. As shown, the desired spectrum is normally generally smooth. However, other spectra may be desired to meet different test requirements. The allowed tolerance in the spectrum is + or − 3 dB. FIG. 6 is a diagrammatic illustration of a typical shock response spectrum produced by impact of a hammer at one end of an untuned resonant beam fixture. As shown, peaks in the spectrum will be produced at the fundamental and harmonic frequencies of the beam, and these will normally be outside the allowed tolerances for a shock response spectrum.

Figure 8:
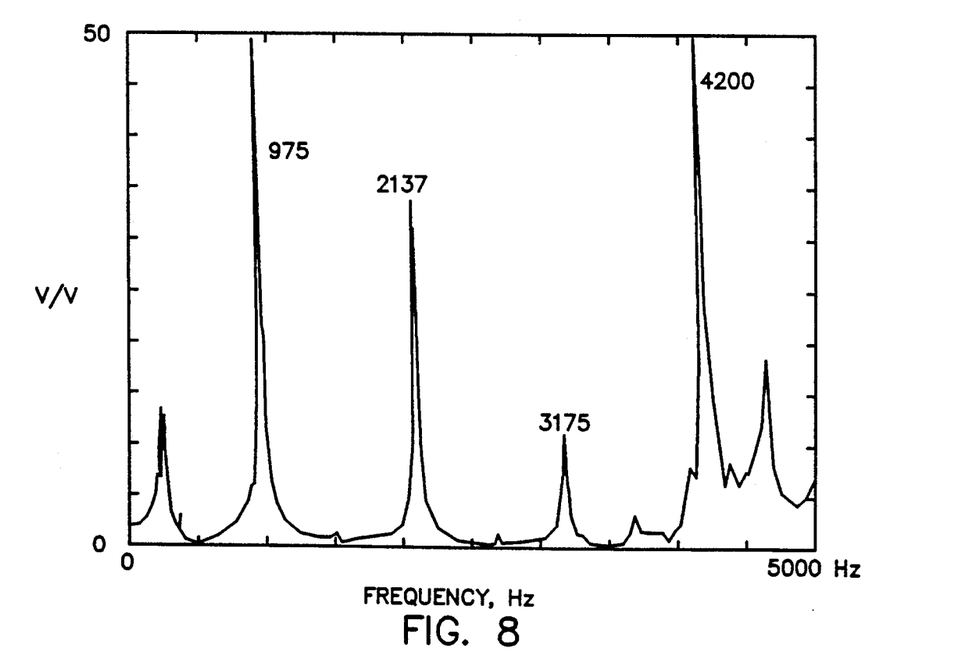
FIG. 8 illustrates the beams dynamic transfer function with no clamps on the beam, showing the fundamental and first three harmonic frequencies of the beam.

The characteristic fundamental resonant frequency and harmonics of the beam can be determined by generating the beam dynamic transfer function as illustrated in FIG. 8. The analysis technique for generating a beam transfer function will be understood by those skilled in the field. The example illustrated in FIG. 8 shows a natural frequency at 975 Hz with harmonics of 2137, 3175, and 4200 Hz. These resonant frequencies will cause peaks in the shock response spectrum, some of which are indicated in FIG. 6. As noted, such peaks are normally undesirable in simulating pyrotechnic shocks and will be outside the allowed variation (tolerances) from the reference shock response spectrum.

Each of the fundamental and harmonic frequencies will have its own specific nodal and anti-nodal positions on the beam. However, it is possible that nodal or anti-nodal positions of one frequency may coincide with those of another frequency. The nodal positions are locations of minimum amplitude at that frequency, i.e. where the magnitude of the imaginary component of the transfer function passes through zero, while the anti-nodal positions are the maximum or peaks at that frequency. Clearly, in order to reduce the amplitude at a particular frequency, the response at that frequency must be damped. Damping can be achieved by positioning masses on the beam at appropriate locations. The approximate clamping positions are determined by node and anti-node locations on the beam for its fundamental and harmonic frequencies.

In order to determine the node and anti-node positions, the input transducer was kept stationary while the response transducer was moved in one inch increments down the length of the beam (77 data collection points). Stored into the array at each point was the magnitude of the imaginary component of the transfer function to 5000 Hz. With all of the data collected, frequencies of the interest could be displayed as imaginary magnitude vs. beam location. FIGS. 12 to 15 illustrate the results of this analysis for one particular beam, a light weight magnesium beam of dimensions 15 by 2 by 77 inches with a 15 by 15 by 6 inch expanded head at the mounting end of the beam. Magnesium alloy was selected for the beam since it requires less energy for excitation than steel or aluminum, and also has excellent damping characteristics.

Figure 12:
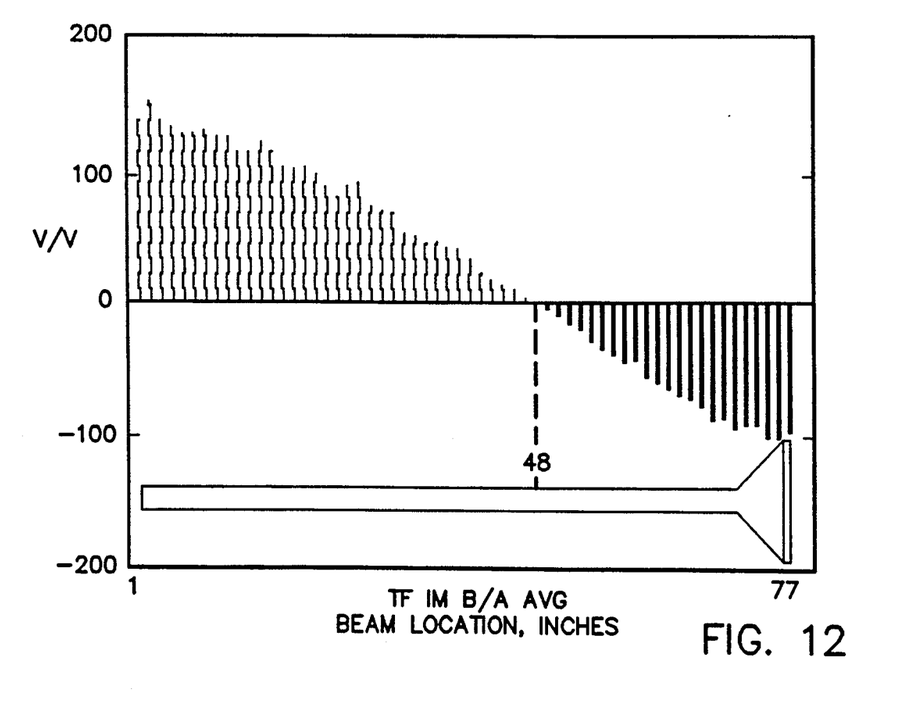
FIGS. 12 to 15 illustrate the location of the nodal and anti-nodal positions at each of the frequencies shown in FIG. 8.
Figure 13:
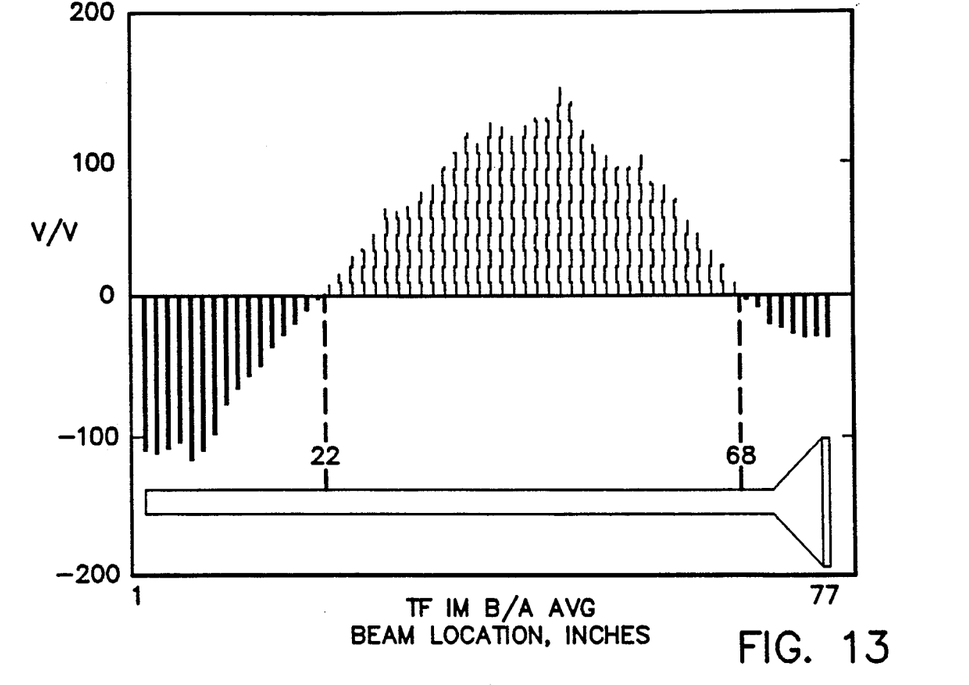
Figure 14:
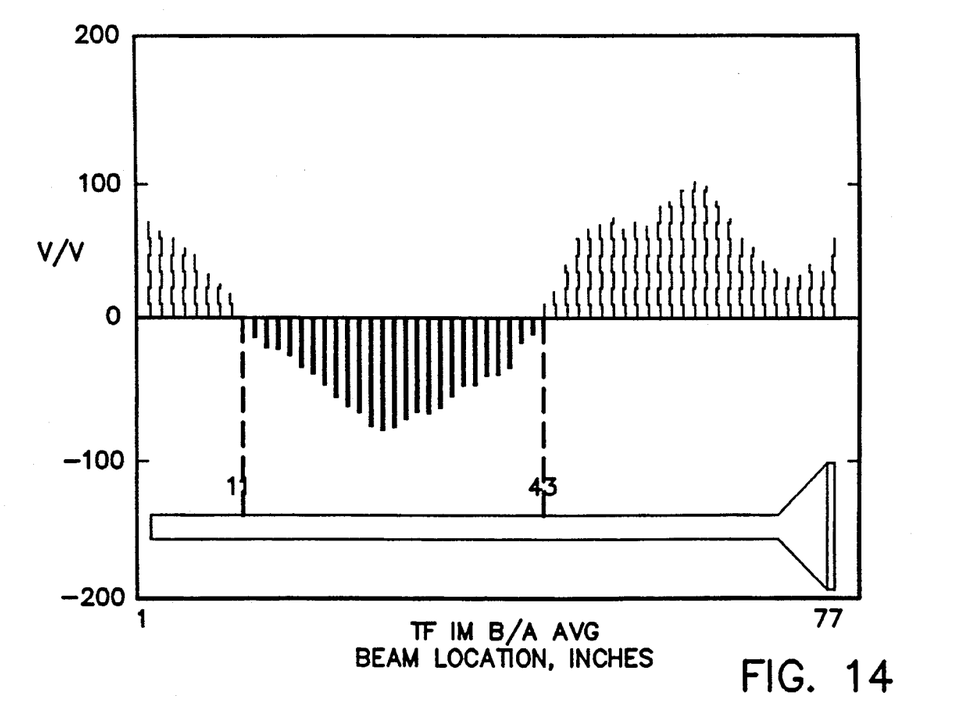
Figure 15:
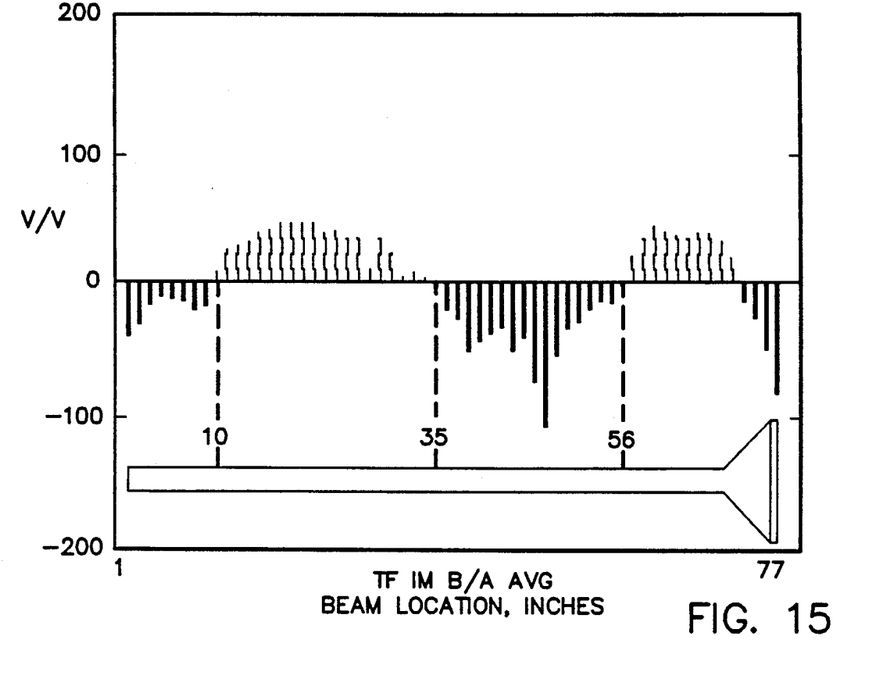

FIG. 12 illustrates the node and anti-node location on the beam at its fundamental frequency of 975 Hz, while FIGS. 13 to 15 illustrate the locations at the harmonic frequencies 2137, 3175, and 4200 Hz, respectively. The approximate node and anti-node locations are tabulated below.

| Mode Frequency (Hz) | Nodes (inches) | Anti-nodes (Inches) |
| --- | --- | --- |
| 975 | 48 | 0,77 |

-continued

| Mode Frequency (Hz) | Nodes (inches) | Anti-nodes (Inches) |
| --- | --- | --- |
| 2137 | 22,68 | 0,45,77 |
| 3175 | 11,43 | 0,27,56,77 |
| 4200 | 10,35,56 | 0,22,46,63,77 |

Clamping at nodal locations has no real effect on the transfer function at that mode frequency. Clamping at or close to the anti-node will dampen the magnitude of the beam response at that frequency. Clamping on the anti-node may dampen the response too much, providing a noticeable dip in the shock response spectrum at that frequency.

Figure 9:
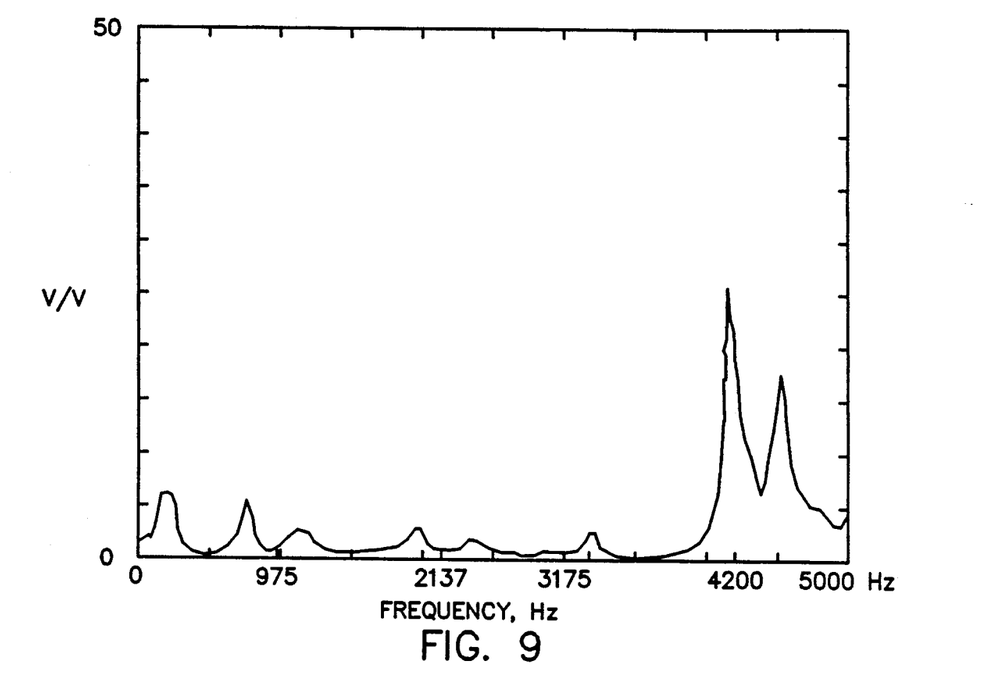
FIG. 9 illustrates the effect on the beams dynamic transfer function when clamps are positioned close to the anti-node positions of the fundamental frequency of 975 Hz.
Figure 10:
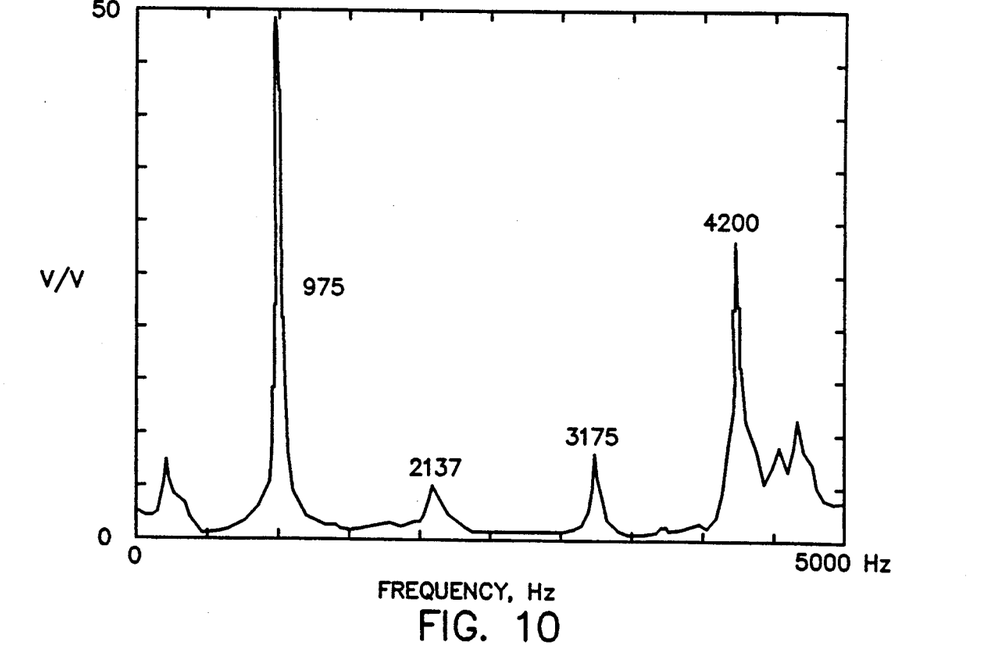
FIG. 10 illustrates the effect of a single clamp close to one of the anti-node positions at 2137 Hz and 4200 Hz.
Figure 11:
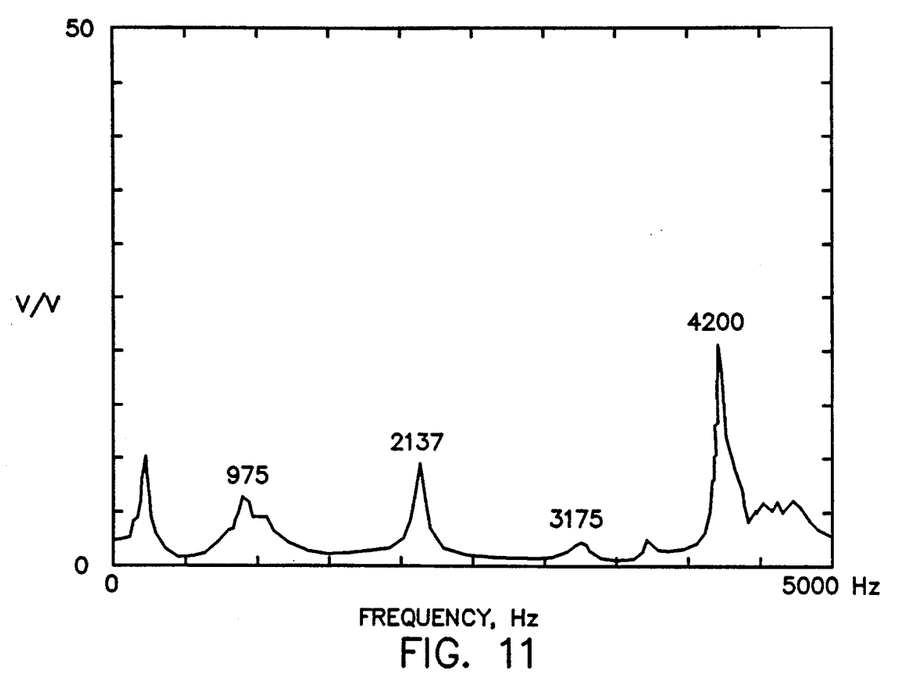
FIG. 11 illustrates the effect of clamps close to anti-node positions at 3175 Hz and 4200 Hz and relatively close to anti-node positions at 975 Hz.

This can be shown with reference to FIGS. 9 to 11, which illustrate the effect on the beam dynamic transfer function of clamping masses at various positions on the particular beam discussed above. As mentioned above, FIG. 8 illustrates the beam transfer function with no clamps. FIG. 9 illustrates the beam transfer function when masses are clamped at opposite ends of the beam, on or around 1 inch and 77 inches. As can be seen from the table above, these correspond to anti-node positions at the fundamental and each of the first three harmonic frequencies. FIG. 9 illustrates the effect of this. As shown, the peak at 975 Hz has been practically eliminated, while the peaks at 2137, 3175 and 4200 Hz are also significantly reduced. Thus, in most cases, clamping on the anti-nodes may produce an undesirable reduction in the response.

However, clamping relatively close to, but not on the anti-node at a particular resonant frequency may reduce the peak sufficiently to maintain it within the desired tolerances. This can be seen on the transfer function in FIG. 10, which illustrates the effect of clamping a single mass at 46 inches on the beam, i.e. close to one of the anti-node positions at 2137 Hz and 4200 Hz. When this diagram is compared with the unclamped transfer function of FIG. 8, it can be seen that the peaks at 2137 and 4200 Hz have been reduced significantly, while the peaks at 975 and 3175 Hz are substantially unaffected. This allows selection of which peaks are to be reduced.

FIG. 11 illustrates the effect on the beams dynamic transfer function when masses are clamped at 28 and 60 inches, i.e. close to anti-node positions at 3175 and 4200 Hz, and relatively close to anti-node positions at 975 Hz. As illustrated, the peaks at 3175 and 4200 Hz are significantly reduced, and some reduction in the peaks at 975 and 2137 Hz is also produced.

With this technique, the beam can be tuned by positioning the clamps to produce the desired reduction in all of the peaks to maintain the spectrum within the desired tolerances.

Figure 7:
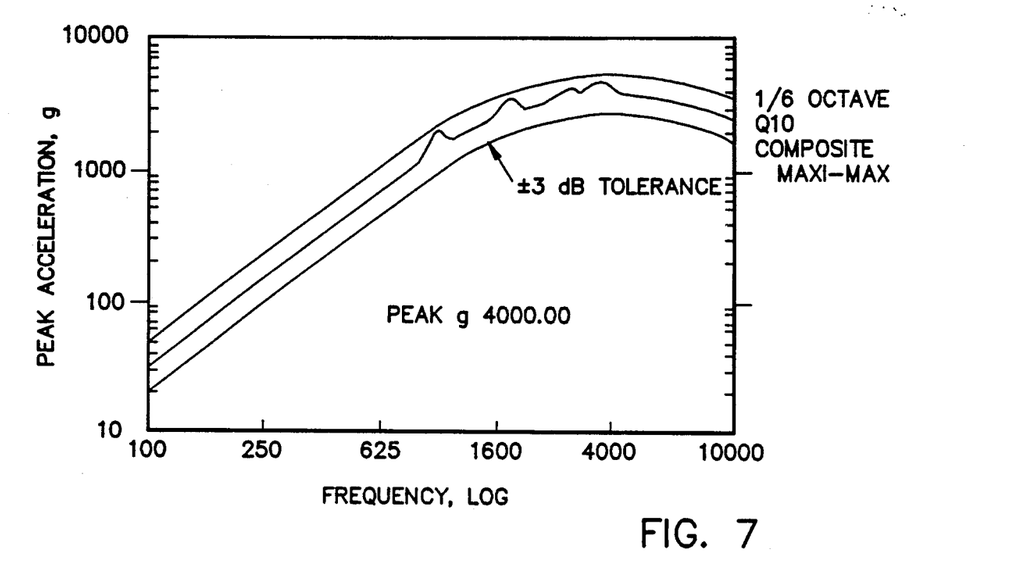
FIG. 7 illustrates a typical shock response spectrum produced by the beam fixture of the apparatus of FIG. 1 after tuning of the beam.
Figure 16:
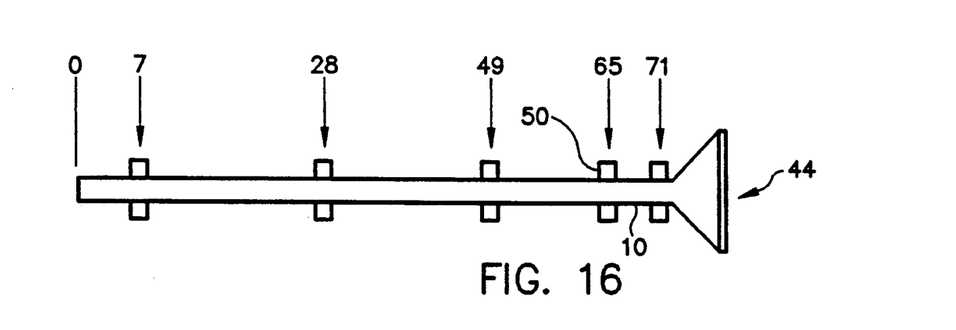
FIG. 16 illustrates the positioning of the clamps on a beam producing the shock response spectrum generally illustrated in FIG. 7.

FIG. 16 illustrates the clamping locations selected for the beam to produce the shock response spectrum illustrated in FIG. 7. Clearly, changing the clamping locations will change the beams frequency response and associated shock response spectrum. In FIG. 16, clamps are located close to but not on at least some of the anti-node locations at each resonant frequency. When clamping close to an anti-node at one particular frequency, care must be taken to ensure that you are not simultaneously positioning a clamp too close to or directly on an anti-node at another frequency, potentially reducing the response at that frequency below the desired limits.

In the example shown in FIG. 16, the clamp at 7 inches will be close to the first anti-node at all of the resonant frequencies shown. The clamp at 28 inches is close to an anti-node at 3175 Hz. The clamp at 49 inches is close to anti-nodes at 2137 and 4200 Hz, the clamp at 65 inches is close to anti-nodes at 975 and 4200 Hz, and the clamp at 71 inches is close to anti-nodes at all frequencies. Once the approximate clamp locations have been determined in this manner, clamps are appropriately positioned on the beam and a shock response spectrum is generated to determine the effect of the clamps on the response. Generally, the peaks at the resonant frequencies will be reduced. The positioning of the clamps can then be adjusted or tuned until the desired response is achieved. FIG. 7 illustrates the response spectrum achieved with all the clamps positioned as shown in FIG. 16. As can be seen, all the peaks have been reduced to within the 3 dB tolerance lines.

The clamps used in this example were 2 by 2 by 17 inch aluminum bars. Good physical contact between the bars and beam is essential. The bar width is kept as small as possible to allow the clamp to be precisely located. If the bars were wider, control of the response would be less easy to achieve, since they would affect a greater region of the beam and thus it would be difficult to ensure that they did not overlap any of the anti-node positions. The use of an adapter or extension plate to mount the test component leaves the entire length of the beam free for positioning clamps. If the component was mounted on the end of the beam itself for x- and y direction testing, it would take up a significant area of the beam, making it unavailable for clamping and beam response tuning, and would itself affect the response.

This system allows the shock response spectrum to be adjusted or tuned by altering the clamp positions on the beam, and also by changing the hammer release height, which will change the amplitude of the response, a higher amplitude being achieved when the hammer release height or angle is increased. Even higher amplitudes may be achieved with alternative impact devices, for example, where a projectile is "fired" into the impact plate at the end of the beam.

Another technique for varying the response is to change the hammer weight. As noted above, a series of different weight hammers is provided, with the operator selecting a particular weight for use in the specific test series being conducted. Generally, heavier weight hammers will increase the impact duration and lower the frequency of the response, while lighter hammers will have the opposite effect. In the specific example described above producing the SRS shown in FIG. 7, a 16 lb. hammer was used. A heavier hammer would shift the response in FIG. 7 to the left, while a lighter hammer would shift it to the right. The impulse waveform and duration can also be changed by altering the impact material and its geometry. The example above utilizes a steel on aluminum impact, which will be of short duration. The duration could be lengthened by changing the material at the end of the beam to rubber or lead. Composite materials or materials of non-solid, honeycomb structure may also be used to control the impulse waveform and duration.

This system therefore allows a significant degree of adjustment in the shock response spectrum to be made relatively easily, allowing the system to be set up to achieve a wide range of alternative desired shock response spectra of the type generally used in pyrotechnic shock testing. The system is less expensive, safer and more convenient than using actual explosives, or an electrodynamic shaker for such testing, and has better repeatability and controllability than both explosive and electrodynamic shaker testing.

Although a preferred embodiment of the invention has been described above by way of example only, it will be understood by those skilled in the field that modifications may be made to the disclosed embodiment without departing from the scope of the invention, which is defined by the appended claims.

We claim:

1. A shock testing apparatus, comprising:
   an elongate beam;
   suspension means for suspending the beam for movement in a longitudinal direction;
   impact means for impacting one end of the beam with a controllable impact velocity;
   mounting means at the opposite end of the beam for mounting a component to be tested in three different perpendicular orientations relative to the beam, the orientations corresponding to perpendicular x and y axis directions in a plane parallel to the component base and a z axis direction normal to the component base;
   sensing means for sensing the oscillation of the beam as a result of impact by the impact means;
   control means for controlling the impact velocity;
   and damping means clamped at predetermined positions on the beam to produce a predetermined shock response spectrum on impact by the pendulum means.

2. The apparatus as claimed in claim 1, wherein the damping means comprise masses clamped close to but not on at least some of the anti-node positions of the fundamental beam resonant frequency and at least one harmonic frequency.

3. The apparatus as claimed in claim 2, wherein the masses are clamped on the beam at positions close to but not on at least some of the anti-node positions of the fundamental and three harmonic frequencies.

4. The apparatus as claimed in claim 1, wherein said impact means comprises a pendulum and said control means comprises drive means for driving said pendulum to a predetermined height and release means for releasing the pendulum when the predetermined height is reached.

5. The apparatus as claimed in claim 4, including braking means for stopping the pendulum after impact with the beam.

6. The apparatus as claimed in claim 5, in which the control means includes means for automatically actuating the braking means at a predetermined interval after impact.

7. The apparatus as claimed in claim 4, including adjustment means for adjusting the height at which the pendulum is released.

8. The apparatus as claimed in claim 4, wherein said control means includes means for stopping the drive means when a predetermined maximum or minimum height is reached.

9. The apparatus as claimed in claim 4, including a support frame adjacent said one end of the beam, said pendulum comprising a pendulum arm suspended at one end from the support frame, and a hammer mounted on the free end of the arm.

10. The apparatus as claimed in claim 9, wherein the hammer is releasably mounted on the pendulum arm, and a plurality of hammers of different weights are provided for selectively mounting on the arm.

11. The apparatus as claimed in claim 9, wherein the support frame includes a rotatable shaft from which the pendulum arm is suspended, the drive means comprises a reversible motor for rotating the shaft in opposite directions, and the control means includes a detector for detecting the rotation of the shaft, and comparator means for comparing the shaft rotation with a preselected degree of rotation corresponding to the selected release height.

12. The apparatus as claimed in claim 4, wherein said release means includes at least one manually operable switch for releasing the pendulum when the predetermined height is reached.

13. The apparatus as claimed in claim 12, including two manually operable switches for simultaneous operation to release the pendulum, the control means further including means for stopping the drive means and enabling the switches when the predetermined height is reached.

14. The apparatus as claimed in claim 1, wherein the beam is of magnesium.

15. The apparatus as claimed in claim 1, wherein said one end of the beam and said impact means are of different materials.

16. The apparatus as claimed in claim 1, including an impact plate secured at said one end of the beam for impact by said impact means.

17. The apparatus as claimed in claim 16, wherein said impact plate and impact means are of the same material.

18. The apparatus as claimed in claim 17, wherein said impact plate and impact means are of steel.

19. The apparatus as claimed in claim 16, wherein said impact plate and impact means are of materials having different hardness.

20. The apparatus as claimed in claim 1, wherein the beam has an enlarged end face transverse to the beam longitudinal axis at the mounting end of the beam, the mounting means comprising z-axis fastener means for mounting a component on the end face with its base perpendicular to the end face, and extension plate means for securing to the end face of the beam with its plane aligned with the beam longitudinal axis, the extension plate means including x and y-axis fastener means for mounting the test component on the extension plate in two perpendicular directions rotated 90 degrees about the z-axis.

21. A method of simulating a predetermined pyrotechnic shock spectrum for pyrotechnic shock testing, comprising the steps of:
suspending a resonant beam for longitudinal movement;
positioning an impact device for impact with one end of the beam;
mounting sensors at the opposite end of the beam for detecting movement of the beam as a result of impact with the impact means;
impacting the first end of the beam with the impact means and analyzing the beam response at spaced locations along the beam to determine the node and anti-node locations of the fundamental resonant frequency and at least one harmonic frequency;
placing damping masses on the bar at locations close to but not on at least some of the determined anti-node locations;
impacting the beam and determining the shock response spectrum from the sensor outputs;
tuning the beam by adjusting the position of the masses until a desired shock response spectrum is produced;
clamping the masses at the adjusted positions;
mounting test components in predetermined orientations on the mounting end of the beam for testing;
impacting the first end of the beam as required to shock test each test component in each of the desired orientations.

22. A shock testing apparatus, comprising:
an elongated beam;
suspension means for suspending the beam for movement in a longitudinal direction;
impact means for impacting a first end of the beam, the impact means comprising a pendulum; mounting means at the opposite end of the beam for mounting a component to be tested;
sensing means for the oscillation of the beam as a result of impact;
drive means for driving the pendulum to a predetermined height; and
control means for releasing the pendulum when the predetermined height is reached.

23. The apparatus as claimed in claim 22, including adjustment means for adjusting the height at which the pendulum is released.

24. The apparatus as claimed in claim 22, wherein said control means includes sensing means for sensing the height of the pendulum and comparator means for comparing the sensed height with a predetermined pendulum release height.

25. The apparatus as claimed in claim 24, further including braking means for stopping the pendulum, said control means including means for switching off the drive means and activating the braking means when the predetermined height is reached.

26. The apparatus as claimed in claim 25, wherein said control means further comprises manually operable switch means for releasing the braking means to drop the pendulum when the predetermined height is reached.

27. The apparatus as claimed in claim 26, wherein the manually operable switch means comprises at least two switches which must be actuated simultaneously to release the braking means.

* * * * *